United States Patent
Higham

(10) Patent No.: US 7,554,449 B2
(45) Date of Patent: *Jun. 30, 2009

(54) METHOD AND APPARATUS FOR PREPARING AN ITEM WITH AN RFID TAG

(75) Inventor: John Higham, Menlo Park, CA (US)

(73) Assignee: Omnicell, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/736,508

(22) Filed: Apr. 17, 2007

(65) Prior Publication Data

US 2007/0285242 A1    Dec. 13, 2007

Related U.S. Application Data

(63) Continuation of application No. 11/187,381, filed on Jul. 21, 2005, now Pat. No. 7,218,231.

(60) Provisional application No. 60/592,843, filed on Jul. 29, 2004.

(51) Int. Cl.
    *G08B 13/14* (2006.01)
(52) U.S. Cl. .................. 340/572.1; 340/571; 340/572.5; 340/10.1; 340/10.51; 198/502.1
(58) Field of Classification Search ............... 340/572.1, 340/571, 572.5, 10.1, 10.51; 198/502.1; 235/383, 462.01, 492
    See application file for complete search history.

(56) References Cited

U.S. PATENT DOCUMENTS

| | | | |
|---|---|---|---|
| 5,962,834 A | 10/1999 | Markman | |
| 6,371,375 B1 | 4/2002 | Ackley et al. | |
| 6,429,776 B1 | 8/2002 | Alicot et al. | |
| 6,484,886 B1 | 11/2002 | Isaacs et al. | |
| 6,539,280 B1 | 3/2003 | Valiulis et al. | |
| 6,597,465 B1 | 7/2003 | Jarchow et al. | |
| 6,617,960 B1 | 9/2003 | Fischer et al. | |
| 6,641,042 B1 | 11/2003 | Pierenkemper et al. | |
| 6,677,852 B1 | 1/2004 | Landt | |
| 6,687,293 B1 | 2/2004 | Loyer et al. | |
| 6,700,931 B1 | 3/2004 | Lee et al. | |
| 6,706,989 B2 * | 3/2004 | Hunter et al. | 209/577 |
| 6,708,879 B2 | 3/2004 | Hunt | |
| 6,712,276 B1 | 3/2004 | Abali et al. | |
| 6,721,391 B2 | 4/2004 | McClelland et al. | |
| 6,982,640 B2 * | 1/2006 | Lindsay et al. | 340/540 |

(Continued)

OTHER PUBLICATIONS

Canadian Office Action, dated Oct. 6, 2008, pp. 1-4, Application No. CA 2,574,946.

*Primary Examiner*—Davetta W Goins
(74) *Attorney, Agent, or Firm*—Townsend and Townsend and Crew LLP

(57) ABSTRACT

An automated reading system for associating an RFID tag and product information includes a conveyor belt for moving a product having an RFID tag and a bar code. The system also includes an RFID scanner and a bar code scanner for reading information on the product as it travels down the conveyor belt. A collecting device is used for receiving the product, and a computer having a database is used for recording the association between the RFID tag and the product information.

12 Claims, 1 Drawing Sheet

U.S. PATENT DOCUMENTS

| | | |
|---|---|---|
| 7,121,457 B2 * | 10/2006 | Michal, III .................. 235/375 |
| 2002/0139846 A1 | 10/2002 | Needham et al. |
| 2002/0170961 A1 | 11/2002 | Dickson et al. |
| 2003/0024975 A1 | 2/2003 | Rajasekharan |
| 2003/0067381 A1 | 4/2003 | Mitchell et al. |
| 2003/0132853 A1 | 7/2003 | Ebert |
| 2003/0139968 A1 | 7/2003 | Ebert |
| 2003/0144985 A1 | 7/2003 | Ebert |
| 2003/0155413 A1 | 8/2003 | Kovesdi et al. |
| 2003/0183697 A1 | 10/2003 | Porter |

* cited by examiner

METHOD AND APPARATUS FOR PREPARING AN ITEM WITH AN RFID TAG

CROSS REFERENCE TO RELATED APPLICATIONS

This application claims the benefit of U.S. Provisional Application No. 60/592,843, filed Jul. 29, 2004, the complete disclosure of which is herein incorporated by reference.

BACKGROUND OF THE INVENTION

In the healthcare industry, the availability of supply products is critical. Various systems exist that provide tracking of product usage, quick replenishment, user tracking, and patient tracking for billing purposes.

In addition, closed cabinet systems exist that prevent the removal of items without the entry of necessary data to perform the above tracking and prevent diversion or theft. Such a system is particularly applicable to the expensive items that are used in an operating room (OR) or cath lab. However, closed cabinet systems are also applicable to the high volume diversion of inexpensive items that are useful outside the healthcare facility such as batteries, bandages, shampoos, pens etc., where the user may consider the item too small to be considered "theft."

In developing such systems, the challenge lies in balancing convenience and speed of access along with entering the necessary data to identify the user, the product and the account number or patient. Systems that dispense an individual product in the same manner as a candy machine, while desirable for convenience and security, are usually too expensive, require special packaging, and are not flexible in terms of the various size and configurations of product that need to be stocked in a hospital. They are also not very space efficient, since items are individually spaced and housed.

The use of RFID tags on products presents an opportunity to track individual products without the need for expensive dispensing systems. This is particularly true of expensive product where it is worth incurring the additional expense of applying the RFID tags. RFID tags are not currently available on products like bar codes, and are not likely to be generally available on healthcare products for many years.

BRIEF SUMMARY OF THE INVENTION

Figure 1:
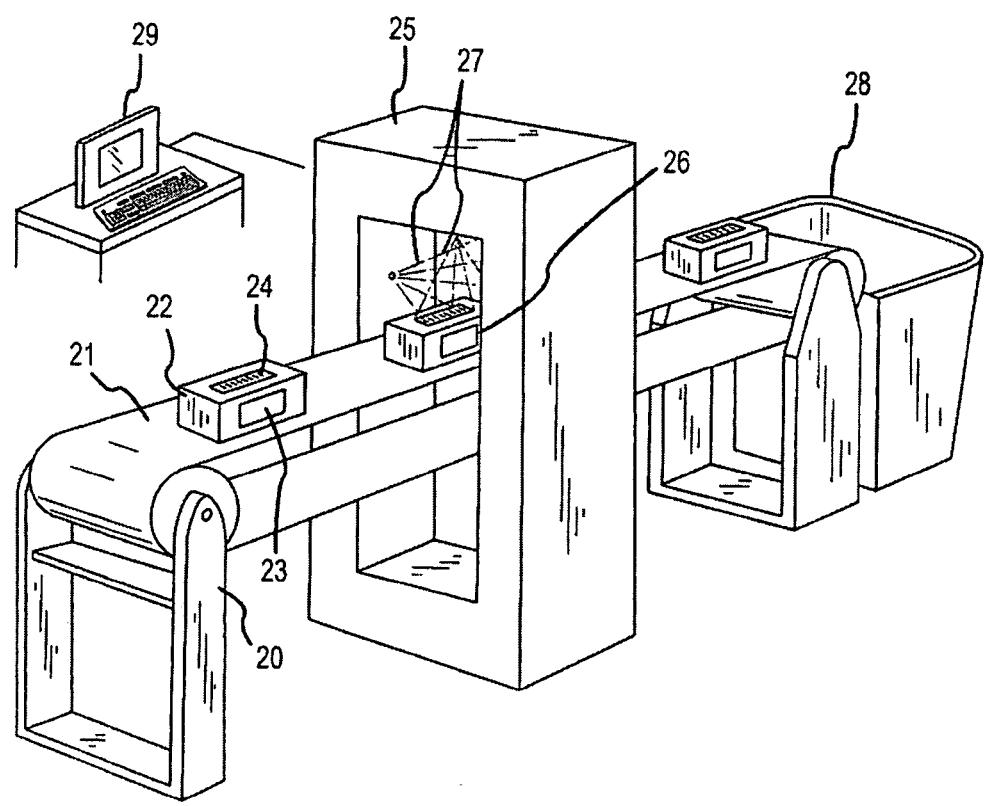
FIG. 1 is a front view of an embodiment of a RFID tag system according to the present invention.

The invention provides both methods and apparatus for the application of RFID tags to an inventory of products in a medical environment. The applied RFID tags provide tracking, monitoring, protecting and safeguarding of the inventory of products when used in conjunction with an RFID cabinet having RFID reading capability. In one embodiment, an RFID tag may be added to a product by affixing the RFID tag to the product. The RFID tag is then read, and the resulting identification information associated with the product using a computer containing a database. Also, various product information may be associated with the identification information from the RFID tag in the database. Examples of product information that may be associated with the identification information includes an internal product ID number used in the hospitals data base, a lot number, a serial number, an expiration date, a UPN or HIBCC bar code or the like. In another embodiment, the invention provides an automatic reading system for associating an RFID tag and product information. The system comprises a conveyor belt for moving a product having an RFID tag and a bar code. The system also includes a first tunnel comprising a first RFID scanner and a first bar code scanner. The first tunnel is positioned above the conveyor belt for reading the RFID tag and the bar code on the product traveling down the conveyor belt. Also, a collecting device is employed for receiving the product, and a computer with an associated database records the association between the RFID tag and the product information. In some cases, a second tunnel having a second RFID scanner and a second bar code scanner may be used as well.

DETAILED DESCRIPTION OF THE INVENTION

Described below are several exemplary embodiments of the invention. Although certain features are described, for ease of discussion, in relation to certain illustrated embodiments, those skilled in the art will appreciate, based on the disclosure herein, that various of the inventive features can be combined in accordance with many different embodiments of the invention. The illustrated embodiments below, therefore, are provided merely by way of example and should not be considered to limit the scope of the invention, which is defined only by the appended claims.

Currently, products for use in the health care industry do not have RFID tags. In accordance with one aspect of the present invention, it is desirable to apply RFID tags to products. In one example, a tag may be used which includes a read-many unique ID. In such cases, the RFID tag may be read and the number associated with a particular product. Prior to the association of a tag with a product, the RFID tags can be applied freely to products—e.g. no particular tag is applied to a particular product. This is useful since relatively unskilled personnel may perform the task of adding the RFID tags to products. In some cases (e.g. liquids and metals), it may be desirable to place a spacer between the tag and the product to raise the tag off the surface.

After the RFID tag is affixed to a product, the tag from each product is read into a database associated with a central computer. The corresponding product information is associated with the appropriate RFID tag and entered into the database. The product information may include, but is not limited to some or all of the following: 1) the internal product ID number used in the hospitals database; 2) the lot number; 3) the serial number; 4) the expiration date; and/or 5) the UPN or HIBCC bar code. Much of the product information may already be in bar code form on the product. For example, the hospital's internal product ID can usually be deduced from the UPN on the product using other hospital databases. Therefore, the process of associating this information with the unique RFID tag number can be a simple scanning process. First, an RFID scanning device scans the RFID tag number. Next, bar code scanning device scans the UPN (retrieving the hospital ID number from another table). Finally, the bar code scanner scans the lot number and serial number (if applicable).

In some cases, the numbers are encoded so that the product information may be deciphered from scanning a single bar code. As such, there is the potential to automate the process. Items with unassociated RFID tags are placed on a conveyor belt. The items pass through a reading tunnel that reads the RFID number. A bar code reading system reads any bar code (s) on the product package. A computer parses the information and associates the RFID number from the RFID tag with the product information from the bar code.

Furthermore, if products of like type pass through at the same time, the computer may be programmed as to which bar codes and which information was expected. This would allow products having missing or suspect information to be diverted into a "re-read hopper" for either re-reading or for manual reading.

In an alternate embodiment, the product may be sent through a second identical conveyor and reading tunnel. The information associated with the product is read a second time. The second reading is checked against information previously read into the database. If there is a discrepancy, the product may be diverted and rejected.

Another aspect of the present invention provides an alarming and alerting capability. In this example, there may be instances where an urgent alarm or alert needs to be issued to alert the user about a specific message associated with the item being dispensed.

FIG. 1 illustrates an automatic reader comprising a product 22, with newly affixed RFID tags 23 and existing bar codes 24. Products are placed on a moving conveyor belt 21, driven by a motor and housing 20. The product enters the reading tunnel 25 where an RFID scanner reads tag 26 and an array of laser readers 27 reads the bar code(s) on the product. The resultant information is transmitted to computer 29, where the information is stored in a database. The product proceeds to a collecting device 28. One embodiment of collecting device 28 comprises two belts at the exit, an accepted belt or rejected belt. A product is directed to either the accepted belt or rejected belt depending upon a good read or bad read respectively.

In yet another embodiment there would be two tunnels, the second tunnel reading the same information as the first tunnel. This information gathered from the second reading using the second tunnel is compared to the first reading using the first tunnel utilizing computer 29. If the two readings do not agree, then the product would be rejected. Computer 29 would use an actuation mechanism to divert that particular product, or remove it from the belt into a re-work hopper. A technician may then examine a product in the re-work hopper and, if necessary, re-label the product.

What is claimed is:

1. A method for associating an RFID identification device with an item, the method comprising:
   operably attaching the RFID identification device to the item;
   reading identification information from the RFID device using a reader;
   transmitting the identification information to a database;
   transmitting item information to the database, wherein the item information is not obtained from the RFID identification device;
   associating the identification information with the item information in the database.

2. A method as in claim 1, further comprising reading the item information from the item prior to transmitting the item information to the database.

3. A method as in claim 2, wherein the item information comprises at least one of an internal product ID number, a lot number, a serial number, an expiration date, a UPN or an HIBCC bar code.

4. A method as in claim 1, further comprising reading the identification information a second time and comparing the identification information from both readers to determine whether they match.

5. A method as in claim 2, further comprising reading the item information a second time and comparing the item information from both readers to determine whether they match.

6. A method as in claim 4, further comprising removing the RFID identification device and replacing it with another one.

7. A method as in claim 1, further comprising moving the item with a conveyor.

8. A method as in claim 7, wherein the RFID identification device is read while the item is on the conveyor.

9. A system for associating an RFID identification device with an item, the system comprising:
   a conveyor configured to move an item along a path;
   an RF reader that is configured to read identification information from an RFID identification device disposed on the item while the item is on the conveyor;
   a scanner that is configured to read an identifier from the item, the identifier having item information;
   a computer having a database for storing and associating a relationship between the identification information and the item information.

10. A system as in claim 9, further comprising at least one of a second RF reader and a bar code scanner, and wherein the computer is configured to compare second readings of the identification information or the item information with the first readings.

11. A system as in claim 9, wherein the scanner comprises a bar code scanner.

12. A method for associating an RFID identification device with an item, the method comprising:
   operably attaching the RFID identification device to the item;
   reading identification information from the RFID device using a reader;
   transmitting the identification information to a database;
   transmitting item information to the database;
   associating the identification information with the item information in the database;
   wherein the item information is unassociated with the RFID identification device both prior to attaching the RFID identification device to the item and reading the identification information from the RFID identification device using the reader.

* * * * *